United States Patent
Münnig et al.

(10) Patent No.: US 10,064,679 B2
(45) Date of Patent: Sep. 4, 2018

(54) ENDOSCOPIC SHANK INSTRUMENT

(71) Applicant: Richard Wolf GmbH, Knittlingen (DE)

(72) Inventors: Sören Münnig, Walzbachtal (DE);
Frank Wehrheim, Bretten (DE);
Stephan Prestel, Rheinstetten (DE);
Philipp Eidner, Bretten-Büchig (DE)

(73) Assignee: Richard Wolf GmbH, Knittlingen (DE)

( * ) Notice: Subject to any disclaimer, the term of this patent is extended or adjusted under 35 U.S.C. 154(b) by 609 days.

(21) Appl. No.: 14/660,123

(22) Filed: Mar. 17, 2015

(65) Prior Publication Data
US 2015/0265340 A1 Sep. 24, 2015

(30) Foreign Application Priority Data
Mar. 18, 2014 (DE) .................. 10 2014 205 006

(51) Int. Cl.
*A61B 18/14* (2006.01)
*A61B 34/00* (2016.01)
*A61B 34/30* (2016.01)
*A61B 17/29* (2006.01)
*A61B 18/00* (2006.01)

(52) U.S. Cl.
CPC ...... *A61B 18/1492* (2013.01); *A61B 18/1445* (2013.01); *A61B 34/30* (2016.02); *A61B 34/71* (2016.02); *A61B 2017/2927* (2013.01); *A61B 2018/00178* (2013.01)

(58) Field of Classification Search
CPC ............ A61B 18/1492; A61B 18/1442; A61B 18/1445; A61B 18/085; A61B 2017/2927; A61B 2018/00184; A61B 2018/00178; A61B 2018/00202; A61B 34/71
USPC .............................................. 606/41, 50–52
See application file for complete search history.

(56) References Cited

U.S. PATENT DOCUMENTS

| | | | |
|---|---|---|---|
| 5,797,900 A | 8/1998 | Madhani et al. | |
| 2004/0162557 A1* | 8/2004 | Tetzlaff | A61B 18/1442 606/51 |
| 2010/0016853 A1* | 1/2010 | Burbank | A61B 18/1445 606/48 |
| 2013/0046337 A1 | 2/2013 | Evans et al. | |

FOREIGN PATENT DOCUMENTS

| | | |
|---|---|---|
| DE | 10 2007 025 084 A1 | 12/2007 |
| DE | 10 2011 075 781 A1 | 11/2012 |
| DE | 10 2011 085 512 A1 | 5/2013 |

* cited by examiner

Primary Examiner — Thomas Giuliani
(74) Attorney, Agent, or Firm — McGlew and Tuttle, P.C.

(57) ABSTRACT

An endoscopic shank instrument has a tool carrier which is arranged at a distal shank end, is bendable relative to the shank and carries a tool. The tool includes at least one electrode which is conductively connectable to a voltage source via an electrical lead led through the shank. The lead is formed by a flexible circuit board in the region of the tool carrier and of the bending of the tool carrier.

2 Claims, 7 Drawing Sheets

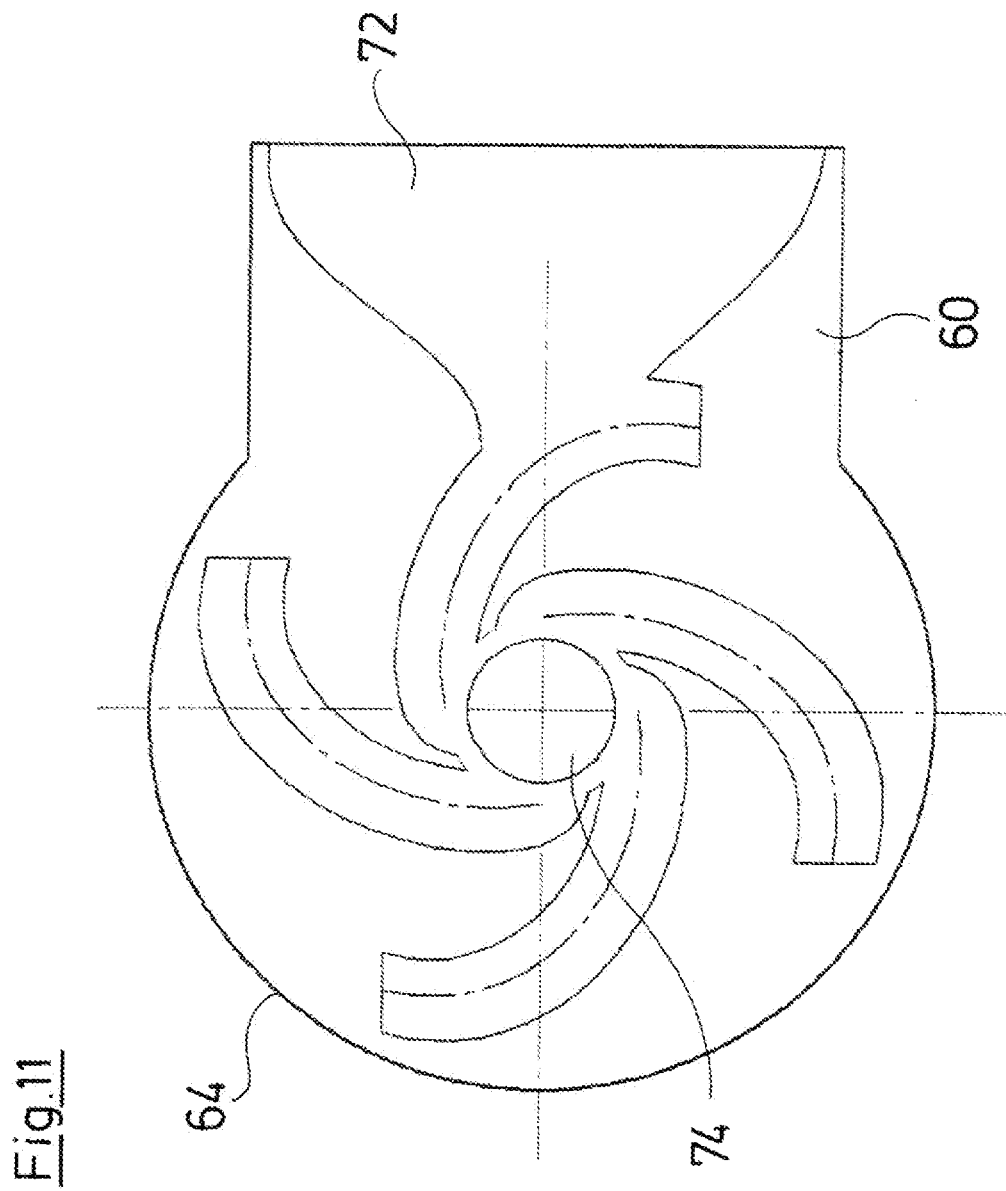

ENDOSCOPIC SHANK INSTRUMENT

CROSS REFERENCE TO RELATED APPLICATIONS

This application claims the benefit of priority under 35 U.S.C. § 119 of German Patent Application 10 2014 205 006.5 filed Mar. 18, 2014, the entire contents of which are incorporated herein by reference.

FIELD OF THE INVENTION

The invention relates to an endoscopic shank instrument with a tool carrier which is arranged at the distal shank end, is bendable relative to the shank and carries a tool having at least one electrode, the electrode being conductively connectable to a voltage source via an electrical lead led through the shank.

BACKGROUND OF THE INVENTION

A multitude of medical treatment methods with which electrical energy is applied in a targeted manner onto body tissue to be treated, has been applied for some time now. Examples of this are coagulation, electrotomy and the ablation of body tissue. These methods are also applied in the field of minimal-evasive surgery. The endoscopic instruments which are applied there usually comprise an elongate shank, on whose distal end a tool is arranged, and this tool is provided with one or two electrodes, depending on whether it is the case of a monopolar or bipolar instrument, and these electrodes can be conductively connected to a voltage source arranged proximally of the shank, via an electrical cable connection led through the shank.

Such instruments, with which a tool carrier carrying the tool and at the distal shank end can be bent relative to the shank and, as the case may be, the tool can also be bent relative to the tool carrier, form the starting point of the invention. It is common to articulately connect the tool carrier to the shank via a joint and to articulately connect the tool to the tool carrier via a further joint, for the bending of the tool carrier and the tool. Different joint mechanisms are used in this context, but these however all lead to a comparatively complex mechanical construction of the instrument in the region of the tool carrier. This complexity is additionally increased due to the fact that guides for the electrical cable connections, via which electrodes arranged on the tool are conductively connectable to a voltage source arranged proximally of the shank, must be provided within the tool carrier. This all has a disadvantageous effect on the cross-sectional size of the instrument, which actually should be kept as small as possible.

SUMMARY OF THE INVENTION

Against this background, it is an object of the invention, to create an endoscopic instrument of the previously described type, which has a simpler and more compact construction compared to known instruments.

With regard to the endoscopic instrument according to the invention, it can be the case of an instrument which is to be actuated manually, as well as an instrument which forms part of a robotic operation system. The instrument comprises an elongate, preferably rigidly designed shank, at whose distal end a tool carrier is arranged. The tool carrier which can be bent relative to the shank carries a tool. This tool or parts of the tool on the tool carrier are preferably movable relative to the tool carrier and are preferably bendable relative to the tool carrier in a plane which corresponds to the bending plane of the tool carrier.

The tool comprises at least one electrode which is conductively connectable to a voltage source via an electrical lead led through the shank.

According to the invention, the electrical lead, via which the electrode is conductively connectable to the voltage source, is formed by a flexible circuit board in the region of the tool carrier and of the bending of the tool carrier relative to the shank. The advantage of this measure lies in the fact that circuit boards can be designed in a comparatively thin-walled manner and have a large design freedom with regard to their shaping, so that the lead connection from the electrode to the voltage source, in the region of the bending of the tool carrier can be adapted to restrictive spatial conditions prevailing there in the best possible manner, and quasi not at all to the radial dimensions of the instrument in the region of the tool carrier and its joint connection to the shank, so that the endoscopic instrument according to the invention can be favorably designed in a slimmer manner than the endoscopic shank instruments of the type being discussed here and which have been known until now.

The flexible circuit board in the known manner can be an electrically insulating, flexible carrier layer for example in the form of a flexible polyimide foil, onto which a strip conductor forming a part of the electrical lead connection of the voltage source and electrode is deposited. This strip conductor due to the higher surface-to-volume ratio can advantageously have a conductive cross section which is significantly smaller than that of the electrical lead cable which has been used until now. The strip conductor, due to the flat construction manner, likewise has an advantageous effect if the electrode arranged on the tool, as is common e.g. with electrosurgical instruments, is conductively connectable to a HF generator as a voltage source, since the skin effect which basically occurs on leads, through which a high-frequency alternating current flows, is reduced to a considerable extent.

The circuit board in the instrument is usefully arranged in a manner such that a preferred bending direction of the circuit board lies parallel to the plane, in which the tool carrier is bendable relative to the shank and, as the case may be, the tool or parts of the tool are bendable relative to the tool carrier. Basically, the circuit board can be designed and dimensioned such that it extends from the tool through the shank up to the proximal instrument end. However, a shorter design of the circuit board is preferably envisaged, with which this circuit board only projects into a distal end section of the shank, where the strip conductor formed on the circuit board is connected for example to a lead cable connected proximally of the shank to the voltage source.

In one advantageous further development of the endoscopic shank instrument according to the invention, one envisages the electrode of the tool being conductively connected to the circuit board via a sliding contact. Accordingly, the circuit board is preferably not fixedly connected to the tool but instead is only in frictional, electrically conductive contact with the electrode of the tool, wherein the circuit board however is usefully positively connected to the tool carrier. The sliding connection of the circuit board to the electrode of the tool is above all advantageous if the tool or a tool part provided with the electrode is movable relative to the tool carrier. Hereby, the conductive connection of the circuit board to the tool via a sliding contact permits relative movements of the tool or of a tool part provided with the electrode, to the circuit board, without this movement resulting in the interruption of the electrically conductive connection of the electrode and the circuit board. The movement of the tool is moreover not prevented or inhibited by the cable which is otherwise used.

With an electrically conductive or lead connection of the electrode provided on the tool, to the circuit board via a sliding contact, it has been found to be particularly advantageous if at least one friction partner of the sliding contact, i.e. the tool or an electrode arranged thereon and/or the circuit board are each provided with a hard gold coating in a contact region with one another. Preferably, a region of the tool which contacts the circuit board and the strip conductor formed thereon, or an electrode arranged on this tool, as well as a region of the circuit board which is in sliding contact with the tool, are preferably coated with hard gold in a surfaced manner, by which means the transition resistance between the strip conductor and the electrode provided on the tool is reduced and the mechanical loadability of the circuit board is increased, above all with regard to the friction occurring between the tool and the circuit board.

With an electrical conductive connection of the electrode provided on the tool to the circuit board via a sliding contact, it is useful to ensure that an interruption or breakage of the conductive connection does not occur due to a relative movement of the tool and the circuit board, counter to the contact direction of the tool and circuit board. For this reason, according to a further advantageous development of the endoscopic shank instrument according to the invention, at least one spring element is provided, by way of which a pressing force is realized in the sliding contact, and which presses the circuit board against the tool in the contact direction of the circuit board and the electrode.

Then, given a bending of the tool carrier relative to the shank, a movement of the circuit board positively connected to the tool carrier relative to the shank occurs if the circuit board is arranged radially distanced to a bending axis of the tool carrier, with which movement the circuit board is moved in the distal direction with respect to the shank. In this context, one advantageously envisages the circuit board in the shank being biased in the axial direction by way of an elastic element which compensates the movement of the circuit board and ensures an electrically conductive connection of the circuit board to a lead cable arranged in the shank.

The tool carrier is usefully designed of an electrically non-conductive material, so that it prevents a flow of current from the electrode to an electrically conductive part of the instrument and/or a flow of current from the electrode to a second oppositely-poled electrode, in order to electrically insulate the electrode which is on the tool and is conductively connected to the voltage source, from electrically conductive parts of the instrument according to the invention, and in particular to electrically insulate two tool parts each provided with an electrode, in the case of a bipolar tool.

Hereby, the tool carrier can basically be designed from any non-conductive material. However, one preferably envisages the tool carrier being formed from polyetheretherketone. The use of polyetheretherketone as a material for the tool carrier is advantageous inasmuch as polyetheretherketone is biocompatible and has a melting temperature which lies above the temperature which is necessary when autoclaving medical instruments.

With regard to the endoscopic instrument according to the invention, it is preferably the case of a bipolar coagulation forceps. Accordingly, the tool of the instrument is preferably a jaw tool with two jaw parts which can be pivoted relative to one another and which are each conductively connected to a circuit board. The instrument in this case thus comprises two circuit boards which bridge the region of the joint connection of the tool carrier to the shank. The jaw parts of the tool are preferably designed in an electrically conductive manner, so that in each case as a whole they form an electrode and are typically insulated to one another on the tool carrier and are preferably arranged spatially separated from one another.

Basically, all control means which are used with known instruments of this type, such as actuation rods or actuation shafts for example in combination with suitable bending mechanisms can be used for the control of the tool carrier and of the jaw parts which are pivotably arranged on the tool carrier. In a manner which is particularly simple with regard to design, pull cables are however used for the control of the tool carrier and for the control of the jaw parts of the jaw part tool, with the shank instrument according to the invention. These pull cables are usefully formed from an electrically non-conductive material, in order not to form an undesired current path in the instrument. In this context, a design of the pull cables from aramide fibres or from ultra-high molecular weight polyethylene fibres is preferred. Hereby, the fact that these fibres have a comparatively high tear resistance and temperature resistance has moreover been found to be advantageous.

With one design of the endoscopic shank instrument according to the invention as a coagulation forceps, it has further been found to be advantageous if the two jaw parts have at least one preferably circular mounting body, via which they are rotatably mounted on a joint pivot provided on the tool carrier, wherein a face side of the mounting body forms a contact surface to a contact region of the circuit board. The jaw parts on their respective mounting body are usefully coupled in movement to the control means which are provided for the pivoting of the jaw parts. Above all, if with regard to the control means it is the case of pull means such as pull cables, then these advantageously engage on the outer periphery of the mounting body, wherein the outer diameter of the mounting body is selected as large as possible, in order to be able to produce an adequate torque for pivoting the jaw part. A comparatively large contact region of the jaw part to the corresponding contact region of the circuit board further advantageously results from this measure. This contact region of the circuit board favorably has a cross section which corresponds to the cross section of the mounting body.

Preferably, at least two electrically conductive contact points which are differently distanced to a center of the contact region of the circuit board are formed on this contact region, although basically only one electrically conductive contact point to the electrically conductive jaw part needs to be formed on the contact region of the circuit board to the contact region provided on the jaw part.

For this purpose, as an alternative to the at least three contact points formed on the contact region of the circuit board, one can also envisage a strip conductor formed on the circuit board running spirally around the center of the contact region of the circuit board at this contact region. This design measure also serves for ensuring the electrical contact of the circuit board and jaw part. Moreover, this design also ensures that worn material of the circuit board and/or jaw part which, as the case may be, arises due to the frictional contact between the circuit board and the jaw part, or other, for example biological substances, are transported to the outside, out of the contact region of the circuit board and jaw part.

A design, with which a strip conductor formed on the circuit board, at the contact region of the circuit board runs around the center of the contact region as a multi-wound spiral has been found to be a further advantageous alternative to the at least three contact points formed on the contact region of the circuit board.

The invention is hereinafter explained in more detail by way of one embodiment which is shown in the drawing. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 11 is a view showing a distal widening of the circuit board according to FIG. 7, according to a third design.

DESCRIPTION OF THE PREFERRED EMBODIMENTS

Figure 1:
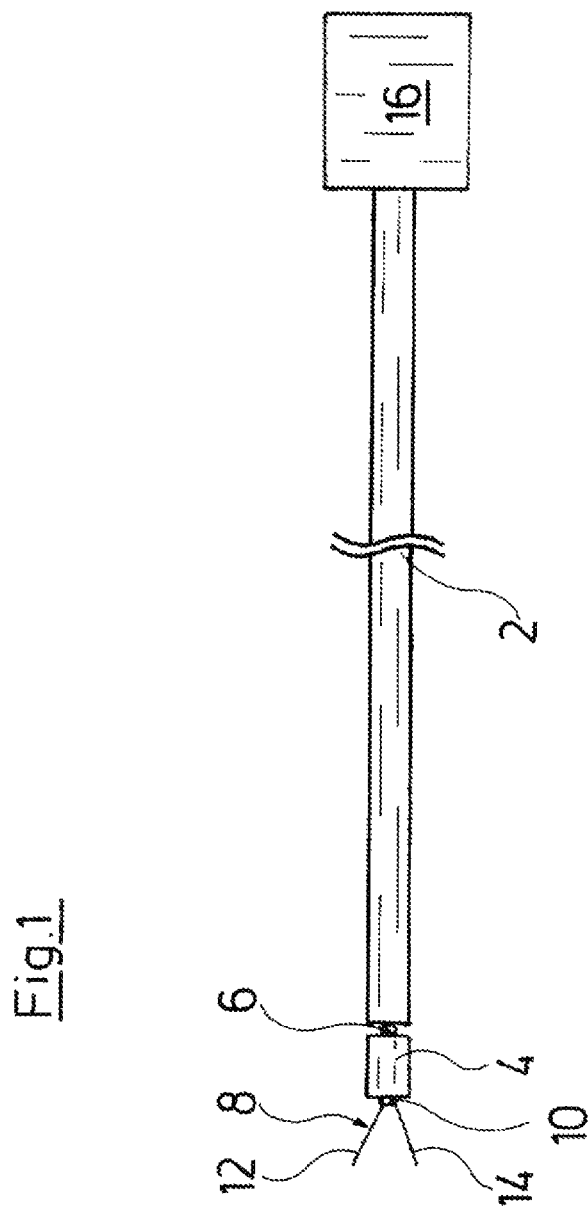
FIG. 1 is a schematically greatly simplified basic view showing an endoscopic shank instrument according to the invention.
Figure 2:
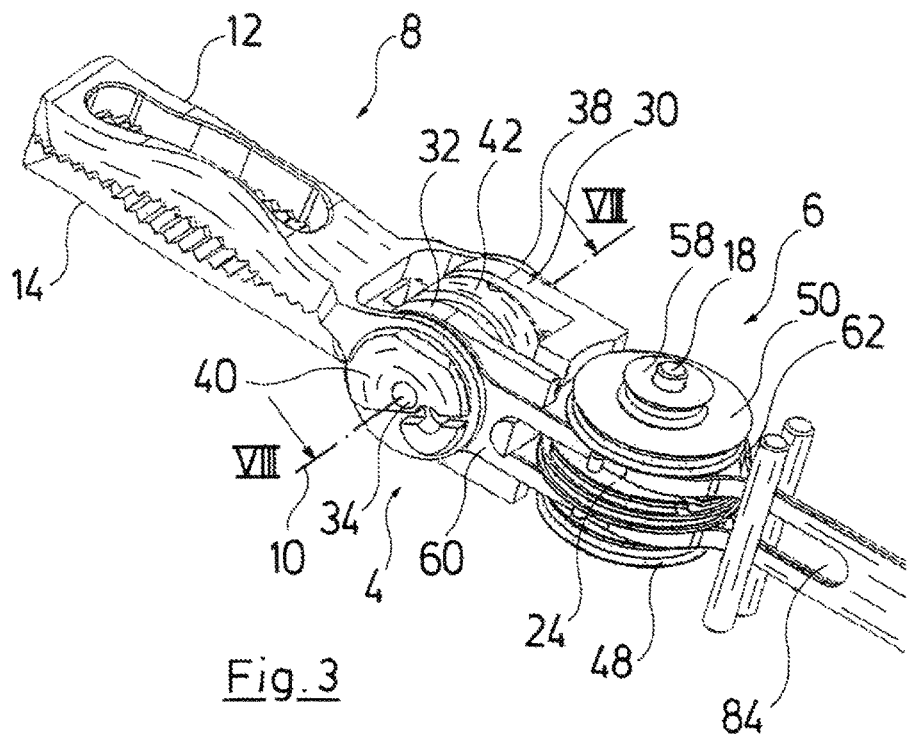
FIG. 2 is a simplified perspective cutaway view showing a distal end region of the endoscopic shank instrument according to the invention, in a view with a representation of the positioning of a circuit board, omitting a pull means for the control of a jaw tool.
Figure 3:
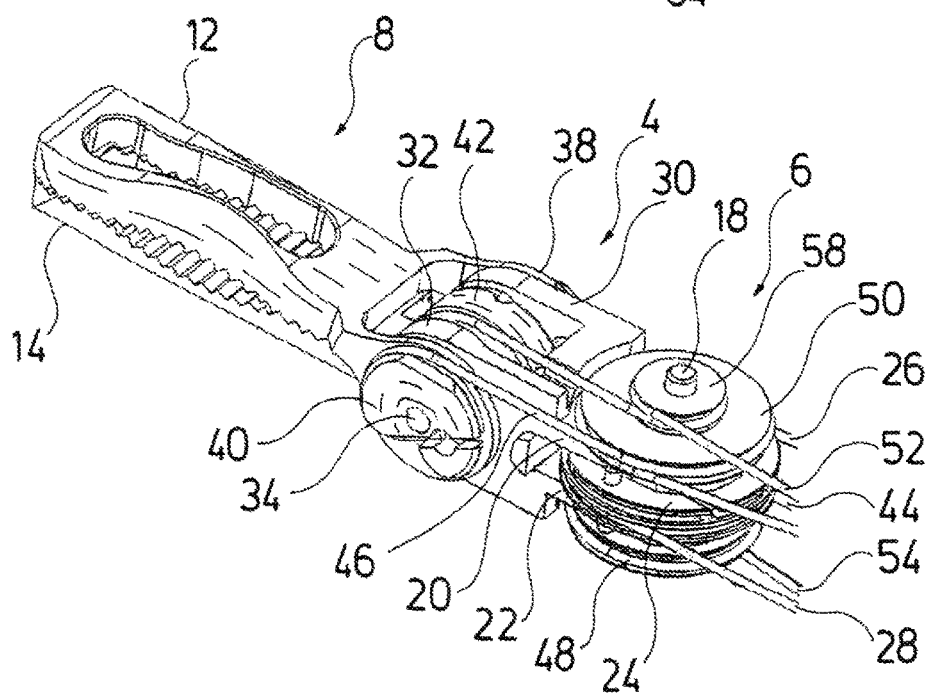
FIG. 3 is a view according to FIG. 2, omitting the circuit board and the representation of pull means for the control of a jaw tool.
Figure 4:
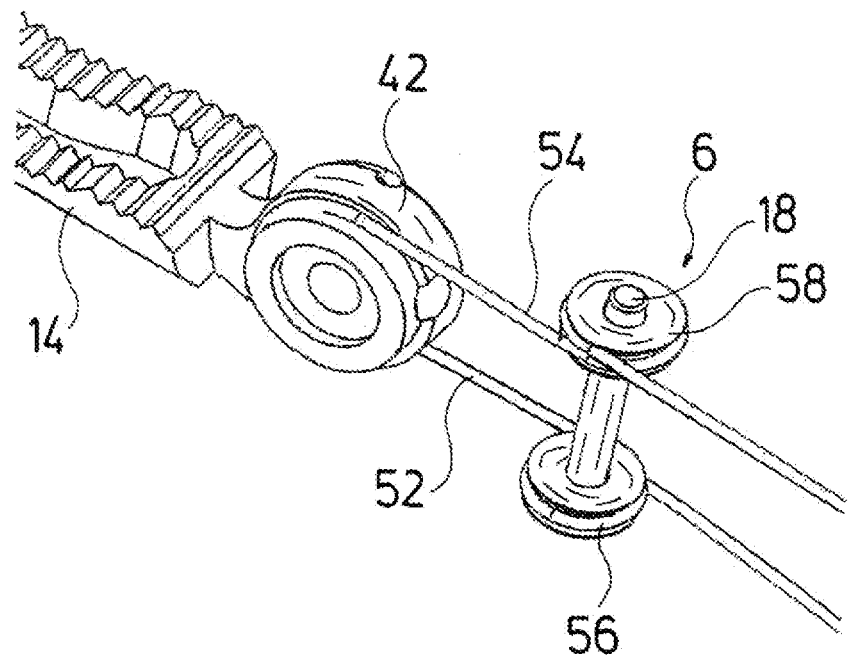
FIG. 4 is a first detail view from FIG. 3.
Figure 5:
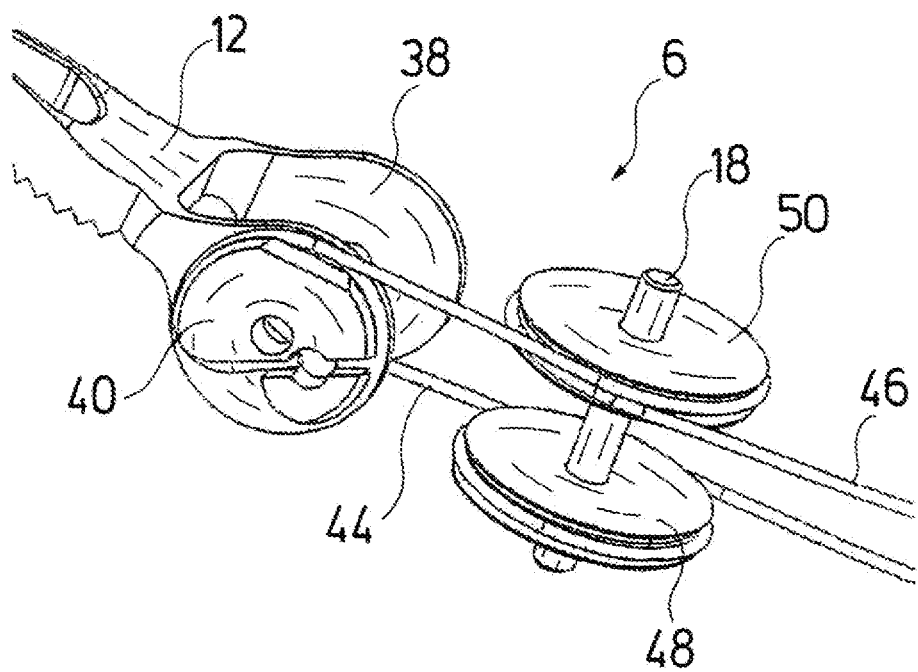
FIG. 5 is a second detail view from FIG. 3.

With regard to the endoscopic shank instrument represented in FIG. 1, it is the case of a coagulation forceps. The coagulation forceps comprises a shank 2 which is designed as a hollow shank and distally of which a tool carrier 4 is arranged. The tool carrier 4 is formed from polyetheretherketone and it is thus not electrically conductive. The tool carrier 4 is bendable relative to the shank 2 via a joint connection 6. At its distal end, the tool carrier 4 carries a jaw tool 8 with two jaw parts 12 and 14 which are pivotable relative to one another about a joint pivot 10. As is explained in more detail hereinafter, the control of the two jaw parts 12 and 14 as well as of the tool carrier 4 is effected via pull cables which are led through the shank 2 to proximally of the shank 2, where they are actively connected to a control device 16. With regard to the control device 16 it can be the case of a handle, as is described e.g. in DE 10 2011 085 512 A1, if the instrument is an instrument which is to be actuated manually. If the instrument forms a part of a robotic operation system, then with regard to the control device 16 it is the case of a control interface of the operating system, as described for example in U.S. Pat. No. 5,797,900 A. The jaw tool 8 serves for the coagulation of body tissue. For this, the two jaw parts 12 and 14 form electrodes which are electrically insulated from one another and which are each connectable to a high frequency (HF) generator as a voltage source, proximally of the shank 2 in the region of the control device 16, by way of a lead led through the shank 2.

As can be deduced from the FIGS. 2 to 6, the joint connection 6 of the tool carrier 4 to the shank 2 is formed by a joint pin 18 which is rotatably mounted on the shank 2 in the region of the distal end of the shank 2. The shank 2 is not represented in the FIGS. 2 to 6 for reasons of a better overview. The tool carrier 4 is connected to the joint pin 18 in a rotationally fixed manner so that the tool carrier 4 is pivoted relative to the shank 2 on rotation of the joint pin 18. The connection of the tool carrier 4 to the joint pin 18 is effected via two projections 20 and 22 which are directed proximally, are formed on the proximal end of the tool carrier 4 and are distanced to one another in the direction of the longitudinal extension of the joint pin 18.

Figure 6:
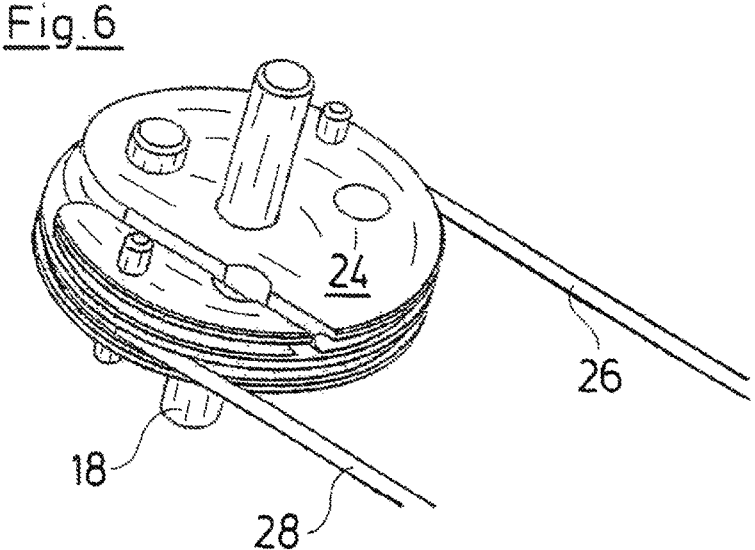
FIG. 6 is a third detail view from FIG. 3.

An actuation roller 24 which is connected to the joint pin 18 in a rotationally fixed manner is arranged on the joint pin 18 for the control of the bending of the tool carrier 4 (see in particular FIG. 6). Two pull cables 26 and 28 are fastened on the actuation roller 24. The fastening of the pull cables 26 and 28 is such that they act antagonistically upon the actuation roller 24 and, entailed by this, act antagonistically upon the tool carrier 4. The actuation roller 24 is arranged on the joint pin 18 such that it engages into the intermediate space between the projections 20 and 22 of the tool carrier 4. The pull cables 26 and 28 which are connected to the actuation roller 24 are led through the shank 2 to its proximal end, where they are actively connected to the control device 16.

Figure 8:
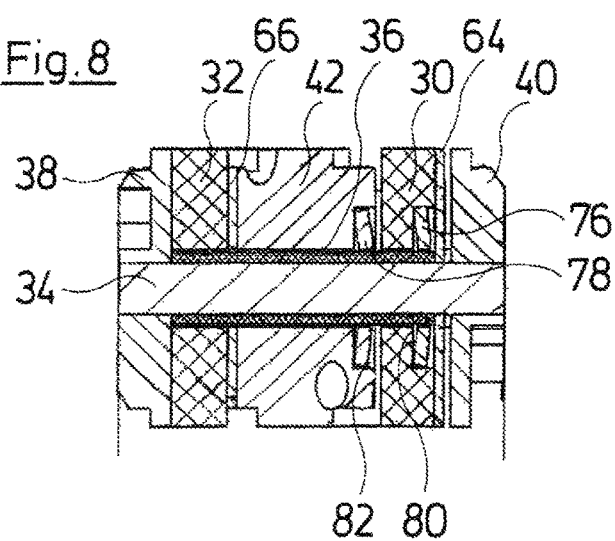
FIG. 8 is a sectional view taken along section line VIII-VIII in FIG. 2.

Two projections 30 and 32 which are distanced to one another in the direction transverse to the longitudinal axis of the joint pin 18 are formed on the distal end of the tool carrier 4. The projections 30 and 32 are connected to one another by way of a pin 34 which forms the joint pivot 10, about which the jaw parts 12 and 14 are pivotable to one another. The pin 34 is led through openings formed on the projections 30 and 32, for fixing the pin 34 on the projections 30 and 32, wherein the two ends of the pin 34 project on the outer side of the outer sides of projections 30 and 32 which are away from one another. The pin 34 is aligned normally to the joint pin 18, so that the jaw parts 12 and 14 are pivotable relative to the shank 2 in a plane normal to the pivot plane of the tool carrier 4. The pin 34, in the region between the two outer sides of the projections 30 and 32 which are away from one another is surrounded by a sleeve 36 of electrically insulating material (FIG. 8).

The jaw part 12 at its proximal end comprises two mounting bodies 38 and 40 which form the proximal end of the jaw part 12, for the rotatable mounting of the jaw part 12 on the pin 34. The essentially circularly designed mounting bodies 38 and 40 are distanced to one another in the direction of the longitudinal extension of the pin 34. The arrangement of the jaw part 12 on the pin 34 is effected in a manner such that the mounting bodies 38 and 40 at the outer side engage around the projections 30 and 32 formed on the tool carrier 4.

The proximal end of the jaw part 14 is formed by a circular mounting body 42 which is likewise essentially circular and via which the jaw part 14 is rotatably mounted on the pin 34, wherein the mounting body 42 engages into the intermediate space between the projections 30 and 32 formed on the tool carrier 4.

A pull cable 44 and 46 is fastened in each case on the outer sides of the respective mounting bodies 38 and 40 which are away from one another, for the movement control of the jaw part 12. These pull cables 44 and 46 are led through the shank 2 to the control device 16 and are actively connected to this. The fastening of the pull cables 44 and 46 on the outer sides of the mounting bodies 38 and 40 is such that they act antagonistically upon the jaw part 12 in the case of tensile loading. The pull cables 44 and 46 in the region of the joint connection 6 of the tool carrier 4 to the shank 2 are guided via deflection rollers 48 and 50 which are rotatably mounted on the joint pin 18 on the outside of the actuation roller 24. The pull cable 44 hereby wraps around the deflection roller 48 and the pull cable 46 wraps the deflection roller 50, by which means it is ensured that the pull cables 44 and 46 are also guided in a defined manner in the region of a bending, even in the case of a bending of the tool carrier 4.

The movement control of the jaw part 14 is effected via two pull cables 52 and 54. These are fastened on the mounting body 42 of the jaw part 14 such that they act antagonistically upon the mounting bodies 42. Pull cables 52 and 54, from the mounting body 42 are led through the shank 2 to the proximal shank end where they are actively connected to the control device 16. The pull cable 42 in the region of the joint connection 6 of the tool carrier 4 to the shank 2 wraps a deflection roller 56 which is rotatably mounted on the joint pin 18 at the outside of the deflection roller 48. In a similar manner, the pull cable 54 wraps around a deflection roller 58 which is rotatably mounted on the joint pin 18 at the outside of the defection roller 50. This guiding of the pull cables 52 and 54 on the deflection rollers 56 and 58 also serves for ensuring a defined guiding of the pull cables 52 and 54 in the region of a bending, even in the case of a bent tool carrier 4. The pull cables 52 and 54, as is also the case with the pull cables 26, 28, 44 and 46, are formed from aramide fibres and are thus very tear-resistant and are electrically non-conductive.

Figure 7:
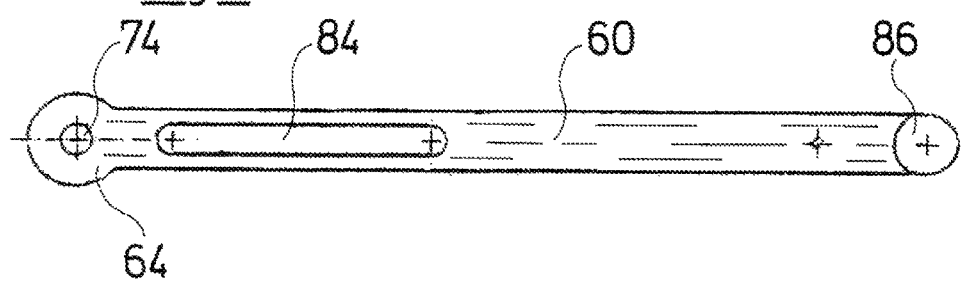
FIG. 7 is a view showing a circuit board from FIG. 2.
Figure 9:
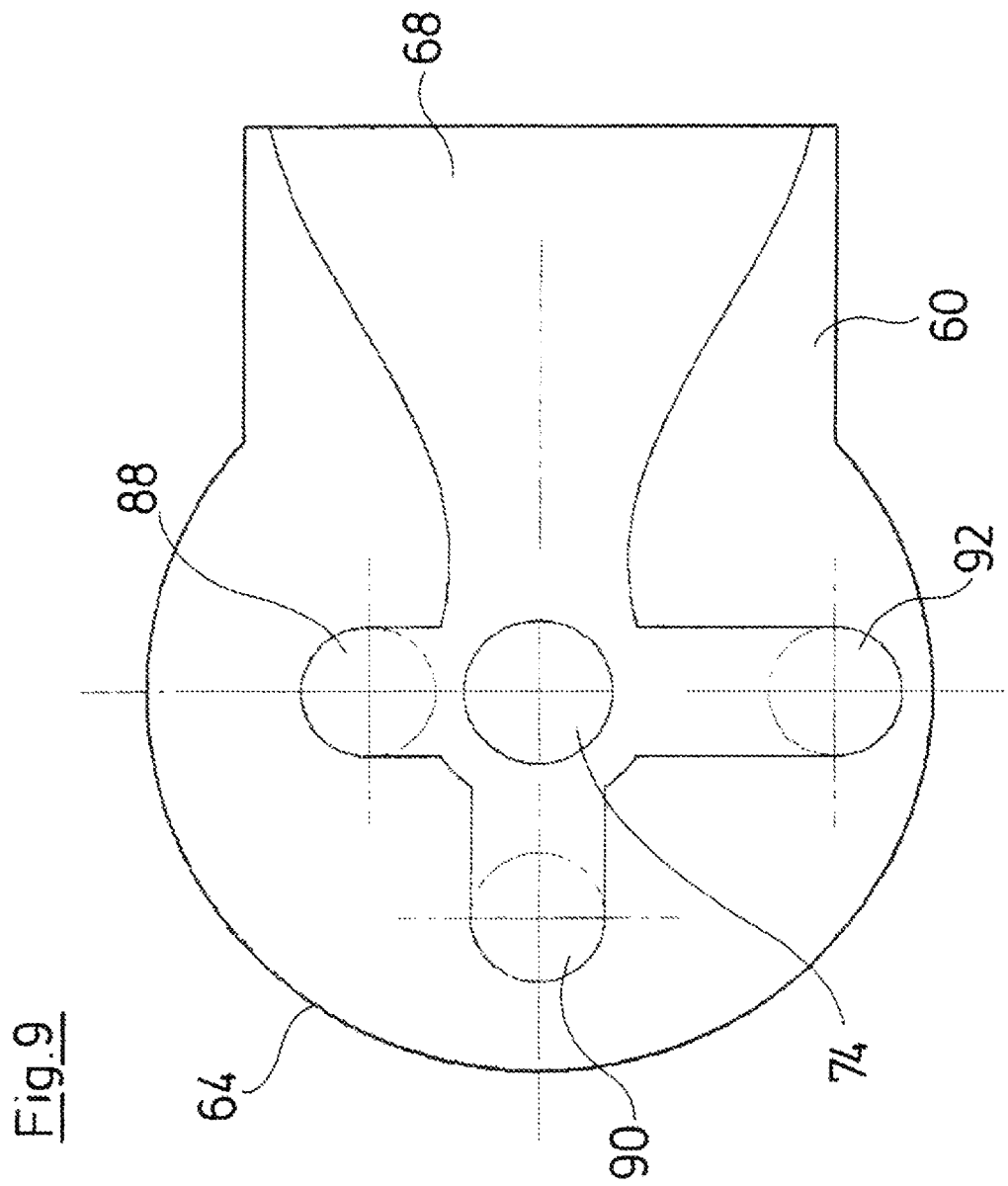
FIG. 9 is a view showing a distal widening of the circuit board according to FIG. 7, according to a first design.
Figure 10:
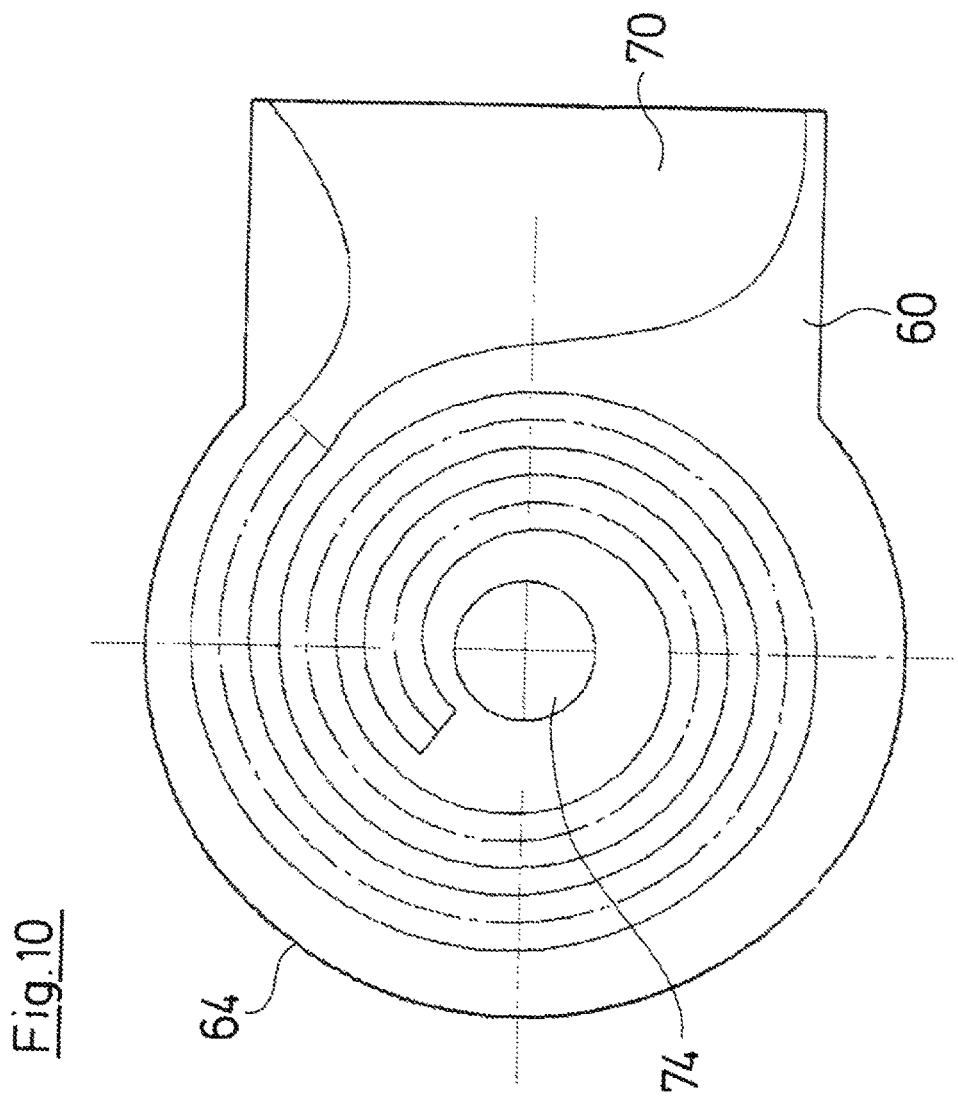
FIG. 10 is a view showing a distal widening of the circuit board according to FIG. 7, according to a second design.

As already mentioned, the two jaw parts 12 and 14 are each electrically conductively connected via a lead to a connection for a HF-generator, said connection provided in the region of the control device 16 but not represented in the drawing. The two leads are each formed by a circuit board 60 and 62 in the region of the bending of the tool carrier 4 relative to the shank 2. The circuit boards 60 and 62, as is evident by way of the circuit board 60 represented in FIG. 7, is designed in an essentially elongate manner, wherein the circuit board 60 at its end which is distal in the installed condition has a circular widening 64, and the circuit board 62 has a circular widening 66. The circuit boards 60 and 62 are designed in a very thin-walled manner and consist of an electrically insulating carrier (substrate) layer in the form of a flexible polyimide foil, into which an electrical strip conductor 68, 70, 72 is embedded (FIGS. 9 to 11). The circuit boards 60 and 62 are designed in a reversely bendable manner in the direction of their wall thickness.

The circuit boards 60 and 62 are fixed on the tool carrier 4, via the widening 64 and 66 respectively which are formed on these circuit boards. An opening 74 serving for receiving the pin 34 is formed on the widenings 64 and 66 in each case for this. On the tool carrier 4, the widening 64 of the circuit board 60 is arranged lying on the mounting body 40 of the jaw part 12 with the flat side, on which the strip conductor 68, 70 and 72 is formed. The widening 64 of the circuit board 60 hereby forms a sliding contact to the mounting body 40 of the jaw part 12 which is rotatable relative to the widening 64 of the circuit board 60. The widening 66 of the circuit board 62 is arranged between the projection 30 formed on the tool carrier 4 and the mounting body 42 of the jaw part, wherein the flat side, on which the strip conductor 68, 70 or 72 is formed, bears on the mounting body 42. The widening 66 of the circuit board 62 forms a sliding contact to the mounting body 42 of the jaw part 14 which is rotatable relative to the widening 66 of the circuit board 62. As is evident from FIG. 8, the radial dimensions of the widening 64 correspond to the radial dimensions of an electrical contact region on the mounting body 40, and the radial dimensions of the widening 66 to the radial dimensions of an electrical contact region on the mounting body 42.

Spring elements 76 and 78 which press the widening 64 of the circuit board 60 onto the mounting body 40 and the widening 66 of the circuit board 62 onto the mounting body 42 (FIG. 8) are provided, in order to ensure an electrically conducive connection of the circuit board 60 to the mounting body 40, and an electrically conductive connection of the circuit board 62 to the mounting body 42. A recess 80 is formed on the projection 30 of the tool carrier 4 at the side of this which faces the mounting body 40 of the jaw part 12, for receiving the spring element 76, with which it is the case of a disc spring. The spring element 78 which is likewise a disc spring is arranged in a recess 82 which is formed on the mounting body 42 of the jaw part 14 on a side which faces the projection 30 of the tool carrier 4.

Departing from the widening 64 and 66, the circuit boards 60 and 62 respectively, at two sides of the joint pin 18 which are away from one another extend in the proximal direction to into a distal end section of the shank 2. Hereby, the actuation roller 24 engages into a longitudinal slide 84 which is formed in each case on the circuit boards 60 and 62. The circuit boards 60 and 62 in the region of the joint pin 18 are deformed in a manner adapted to the geometry of the instrument and are thus arranged in the region of the bending of the tool carrier 4 in an as space-saving as possible manner. The circuit boards 60 and 62, at a contact region 86 formed at the end which is away from the widening 64 and 66 of the circuit boards 60 and 62 respectively, are connected in each case to a lead cable which is not represented in the drawing and which leads to the connection for the HF generator, said connection arranged proximally of the shank 2. The connection of the circuit boards 60 and 62 to the lead cables is hereby effected in each case via a tension spring mounting which is likewise not represented in the drawing.

It is evident from FIGS. 9-11 that the strip conductors 68, 70 and 72 which are deposited on the circuit boards 60 and 62 can differ in the region of the widening 64 and 66 respectively. Thus, the strip conductor 68 which is represented in FIG. 9 ends at three electrically conductive contact points 88, 90 and 92 having a different radial distance to the center of the widening 64 and 66. The strip conductor 70 which is represented in FIG. 10 is designed spiral-shaped in the region of the widening 64 and 66, and the strip conductor 72 represented in FIG. 11 is designed as a multi-wind spiral around the center of the widening 64 and 66, in the region of the widening 64 and 66.

While specific embodiments of the invention have been shown and described in detail to illustrate the application of the principles of the invention, it will be understood that the invention may be embodied otherwise without departing from such principles.

APPENDIX

List of reference numerals

| | |
|---|---|
| 2 | shank |
| 4 | tool carrier |
| 6 | joint connection |

APPENDIX-continued

List of reference numerals

| | |
|---|---|
| 8 | jaw tool |
| 10 | joint pivot |
| 12 | jaw part |
| 14 | jaw part |
| 16 | control device |
| 18 | joint pin |
| 20 | projection |
| 22 | projection |
| 24 | actuation roller |
| 26 | pull cable |
| 28 | pull cable |
| 30 | projection |
| 32 | projection |
| 34 | pin |
| 36 | sleeve |
| 38 | mounting body |
| 40 | mounting body |
| 42 | mounting body |
| 44 | pull cable |
| 46 | pull cable |
| 48 | deflection roller |
| 50 | deflection roller |
| 52 | pull cable |
| 54 | pull cable |
| 56 | deflection roller |
| 58 | deflection roller |
| 60 | circuit board |
| 62 | circuit board |
| 64 | widening |
| 66 | widening |
| 68 | strip conductor |
| 70 | strip conductor |
| 72 | strip conductor |
| 74 | opening |
| 76 | spring element |
| 78 | spring element |
| 80 | recess |
| 82 | recess |
| 84 | longitudinal slot |
| 86 | contact region |
| 88 | contact point |
| 90 | contact point |
| 92 | contact point |

The invention claimed is:

1. An endoscopic shank instrument comprising:
   a shank;
   a tool carrier arranged at a distal shank end of the shank, the tool carrier being movable relative to the shank;
   a tool having at least one electrode, the tool being connected to said tool carrier; and
   a circuit board, said circuit board comprising a substrate and a conductive material in or on said substrate, said conductive material extending from one end of said circuit board to another end of said circuit board, said one end of said circuit board being adjacent said tool carrier and said another end being located in an interior of said shank, said conductive material defining at least one conductive flow path extending from said one end of said circuit board to said another end of said circuit board, wherein said at least one electrode is conductively connectable to a voltage source via said circuit board.

2. An endoscopic shank instrument according to claim 1, wherein said tool carrier comprises a joint pivot, said circuit board comprising a bent portion, said bent portion following a contour of said joint pivot.

* * * * *